(12) United States Patent
Takenaga et al.

(10) Patent No.: US 10,182,218 B2
(45) Date of Patent: Jan. 15, 2019

(54) ENDOSCOPE AND ENDOSCOPIC SYSTEM

(71) Applicant: Panasonic Intellectual Property Management Co., Ltd., Osaka (JP)

(72) Inventors: Yuuichi Takenaga, Fukuoka (JP); Haruyasu Katahira, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/020,617

(22) Filed: Jun. 27, 2018

(65) Prior Publication Data

US 2018/0316899 A1 Nov. 1, 2018

Related U.S. Application Data

(63) Continuation of application No. 15/010,307, filed on Jan. 29, 2016, now Pat. No. 10,038,883.

(30) Foreign Application Priority Data

Mar. 23, 2015 (JP) .................................. 2015-060096

(51) Int. Cl.
*A61B 1/00* (2006.01)
*H04N 9/64* (2006.01)
*G02B 27/14* (2006.01)
*G01J 3/50* (2006.01)
*H04N 9/09* (2006.01)
*H04N 5/378* (2011.01)
(Continued)

(52) U.S. Cl.
CPC ............. *H04N 9/64* (2013.01); *A61B 1/0005* (2013.01); *A61B 1/00009* (2013.01); *A61B 1/00186* (2013.01); *A61B 1/04* (2013.01); *A61B 1/042* (2013.01); *A61B 1/043* (2013.01); *G01J 3/502* (2013.01); *G02B 23/2453* (2013.01); *G02B 27/1013* (2013.01); *G02B 27/126* (2013.01); *G02B 27/141* (2013.01); *H04N 5/232* (2013.01); *H04N 5/378* (2013.01); *H04N 9/09* (2013.01)

(58) Field of Classification Search
CPC .. H04N 9/64; A61B 1/00009; A61B 1/00186; G02B 27/103
USPC .......................................................... 348/71
See application file for complete search history.

(56) References Cited

U.S. PATENT DOCUMENTS 5,777,674 A 7/1998 Ohmuro
5,910,816 A 6/1999 Fontenot et al.
(Continued)

FOREIGN PATENT DOCUMENTS

JP 07-281012 A 10/1995
JP 09-011445 A 1/1997
(Continued)

OTHER PUBLICATIONS

Extended European Search Report, dated Aug. 2, 2016, for corresponding EP Application No. 16152515.9-1666, 6 pages.

*Primary Examiner* — Jeffery A Williams
(74) *Attorney, Agent, or Firm* — Seed IP Law Group LLP

(57) ABSTRACT

Disclosed is an endoscope including: a four-color separation prism configured to separate light from an object into three primary colors of light and infrared light; four image sensors configured to convert optical images of the separated three primary colors of light and an optical image of the separated infrared light into electrical signals; and an output device configured to output the converted electrical signals.

20 Claims, 6 Drawing Sheets

(51) Int. Cl.
*H04N 5/232* (2006.01)
*A61B 1/04* (2006.01)
*G02B 27/12* (2006.01)
*G02B 27/10* (2006.01)
*G02B 23/24* (2006.01)

(56) References Cited

U.S. PATENT DOCUMENTS

2012/0268573 A1\* 10/2012 Schonborn ............ A61B 1/051
　　　　　　　　　　　　　　　　　　　　　348/49
2013/0184591 A1 　7/2013 Tesar

FOREIGN PATENT DOCUMENTS

JP　　　2013-116353 A　　6/2013
WO　　2009/117483 A1　　9/2009

\* cited by examiner

ENDOSCOPE AND ENDOSCOPIC SYSTEM

BACKGROUND OF THE INVENTION

1. Field of the Invention

This disclosure relates to an endoscope and an endoscopic system.

2. Description of the Related Art

In the related art, an endoscopic system in which a three-color separation prism is used is known. An endoscopic system disclosed in Japanese Patent Unexamined Publication No. 2013-116353 acquires a captured color image in which a site in the body is expressed in a combination of three colors, that is, red (R), green (G), and blue (B), and performs image processing on the captured image to emphasize the designated wavelength component.

Meanwhile, when an IR light (infrared light) component is added to an image in addition to the three R, G, and B colors, the image quality of the image captured by an endoscope is not good enough in the endoscopic system disclosed in Japanese Patent Unexamined Publication No. 2013-116353.

SUMMARY OF THE INVENTION

This disclosure is made in light of this problem, and provides an endoscope and an endoscopic system by which it is possible to improve image quality to which an infrared light component is added.

According to an aspect of this disclosure, there is provided an endoscope including: a four-color separation prism configured to separate light from an object into three primary colors of light and infrared light; four image sensors configured to convert optical images of the separated three primary colors of light and an optical image of the separated infrared light into electrical signals; and an output device configured to output the converted electrical signals.

According to this disclosure, it is possible to improve the image quality of an image to which an infrared light component is added and which is captured by an endoscope.

DETAILED DESCRIPTION OF THE PREFERRED EMBODIMENTS

Hereinafter, an exemplary embodiment of this disclosure will be described with reference to the accompanying drawings.

Circumstances for obtaining an exemplary embodiment of this disclosure will be described.

In an operation in which an endoscope is used, a fluorescent substance called indocyanine green (ICG) is injected into the body, and a site (diseased site) (for example, a tumor) containing the excessively accumulated fluorescent substance is irradiated with near-infrared light, and an image of a site containing the diseased site is captured. The ICG is a substance that emits near-infrared fluorescent light having a longer wavelength (for example, light having a peak wavelength of 835 nm) when the ICG is excited by near-infrared light (for example, light having a peak wavelength of 805 nm or 750 nm to 810 nm).

When one-plate camera with one image sensor receives light containing an IR component, and captures an image of a diseased site, a light incident surface of the image sensor is provided with four divided filters for red (R), green (G), blue (B), and IR components. Therefore, it is necessary to increase the size of the image sensor to obtain desired color reproductivity and desired resolution. As a result, a one plate camera can hardly be applied to an endoscope.

Figure 8:
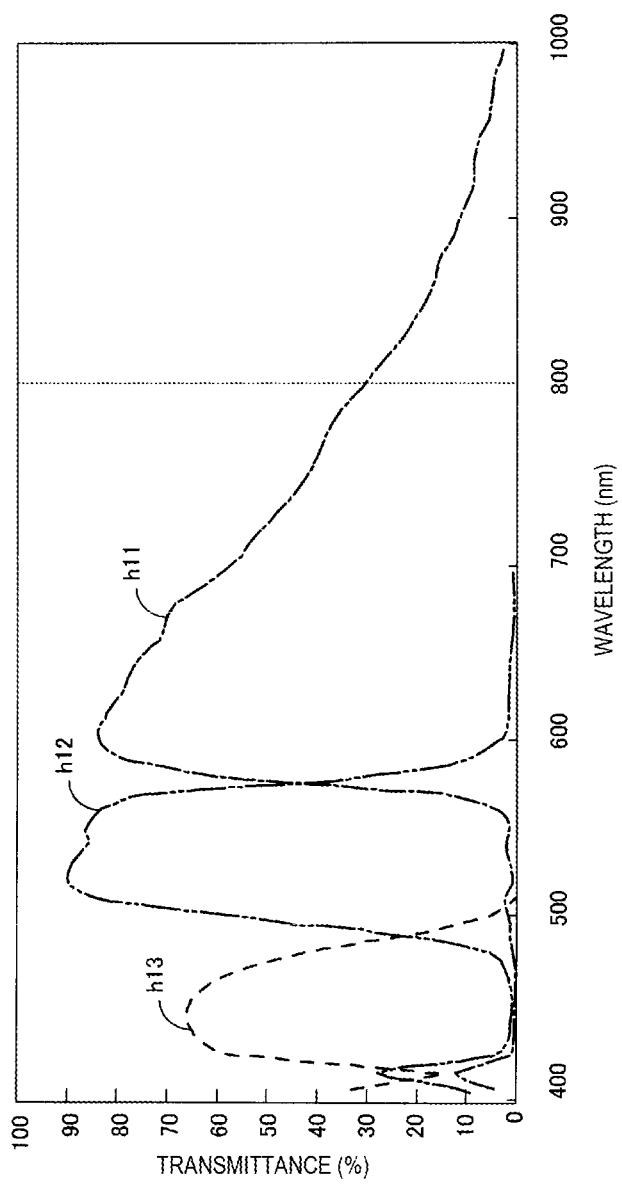
FIG. 8 is a graph illustrating spectral characteristics of a three-color separation prism.

As illustrated in an endoscopic system disclosed in Japanese Patent Unexamined Publication No. 2013-116353, when a three plate camera using a three-color separation prism receives light containing the IR component, and captures an image of a diseased site, as illustrated in FIG. 8, the signal strength of the IR component (for example, light having a wavelength of 800 nm or greater) is low.

FIG. 8 is a graph illustrating spectral characteristics of a three-color separation prism. In FIG. 8, the vertical axis represents the transmittance of each color, and the horizontal axis represents the wavelength. The transmittance is equivalent to a ratio between the amount of light incident to each of prisms for R, G, and B components and the amount of light incident to image elements corresponding to the prisms. h11 represents the transmittance of R component light. h12 represents the transmittance of G component light. h13 represents the transmittance of B component light. h11 also contains the transmittance of IR component light.

As illustrated in FIG. 8, the IR component light is acquired by the image sensor receiving the R component light (refer to the waveform h11), but the transmittance of the IR component (for example, a component having a wavelength of 800 nm or greater) is low compared to the transmittances of the R, G, and B component light. Therefore, the signal strength of the IR component is low, and an image (IR image) obtained using the IR component becomes blurred.

In contrast, when the endoscopic system disclosed in Japanese Patent Unexamined Publication No. 2013-116353 amplifies the IR component to increase the signal strength of the IR component, an image becomes blurred, or noise is emphasized. Therefore, the image quality of an IR image is degraded. Accordingly, it is difficult to observe a desired site (diseased site) containing the IR component in the image obtained using the amplified IR component.

Hereinafter, an endoscope and an endoscopic system by which it is possible to improve image quality of an image to which an infrared light component is added will be described.

The endoscope in the following exemplary embodiments is used to observe a site (object) in the body, for example, in the abdominal cavity.

First Exemplary Embodiment

Configuration of Endoscope

Figure 1:
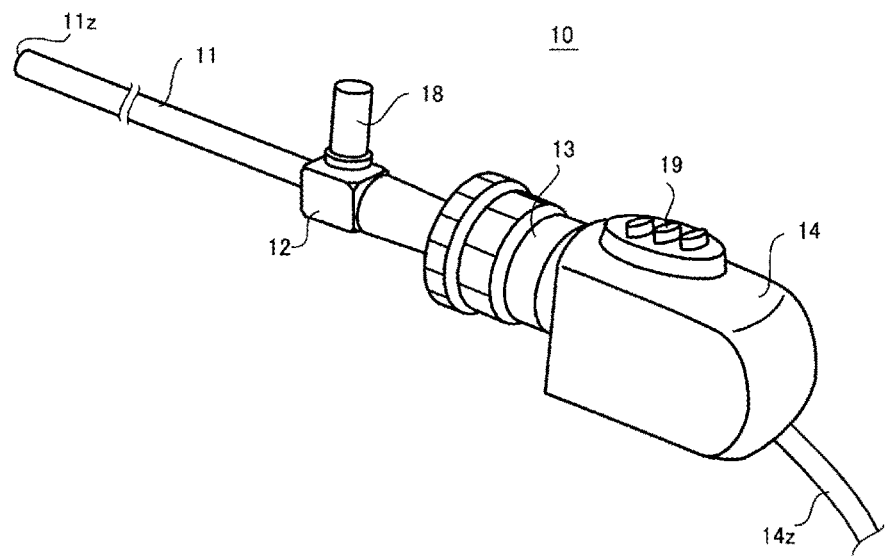
FIG. 1 is an exterior view illustrating an example of an endoscope in a first exemplary embodiment of this disclosure.
Figure 2:
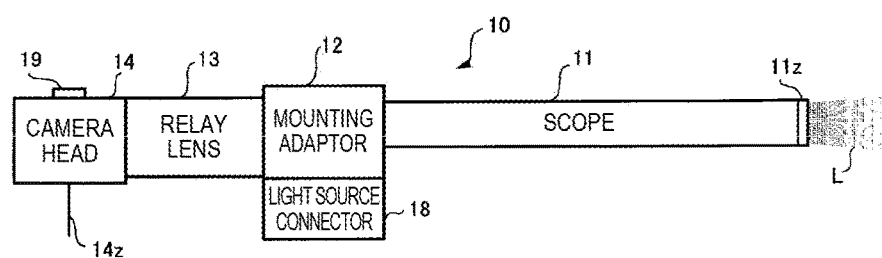
FIG. 2 is a schematic view illustrating an example of the configuration of the endoscope.

FIG. 1 is a schematic view illustrating the exterior of endoscope 10 in a first exemplary embodiment. FIG. 2 is a schematic view illustrating the configuration of endoscope 10. Endoscope 10 is a medical instrument which a user can handle with one hand. Endoscope 10 is configured to include scope 11; mounting adapter 12; relay lens 13; camera head 14; operation switch 19; and light source connector 18.

Scope 11 is a main part of a rigid endoscope, which is inserted into the body, and is an elongated light guiding member capable of guiding light from a proximal end to a distal end thereof. Scope 11 includes image-capturing window 11z at the distal end thereof; an optical fiber through which an optical image incident via the image-capturing window 11z is transmitted; and an optical fiber guiding light L, which is introduced via light source connector 18, to the distal end. Image-capturing window 11z is made of an optical material such as optical glass or optical plastic.

Mounting adapter 12 is a member for mounting scope 11 on camera head 14. Various scopes can be attachably and detachably mounted on mounting adapter 12. Light source connector 18 is mounted on mounting adapter 12.

Light source connector 18 introduces illumination light for illuminating a site (diseased site or the like) in the body from a light source apparatus (not illustrated). The illumination light contains visible light and IR light. Light introduced to light source connector 18 is guided to the distal end of scope 11 via scope 11, and a site (diseased site or the like) in the body is irradiated with the light via image-capturing window 11z. For example, a light source is an LED light source. The light source may be a xenon lamp, a halogen lamp, or the like instead of an LED light source.

Relay lens 13 converges the optical image, which is transmitted via scope 11, on an image-capturing surface. Relay lens 13 includes multiple lenses, and adjusts the focal point and the magnification ratio by moving the lenses according to the amount of operation of operation switch 19.

Figure 5:
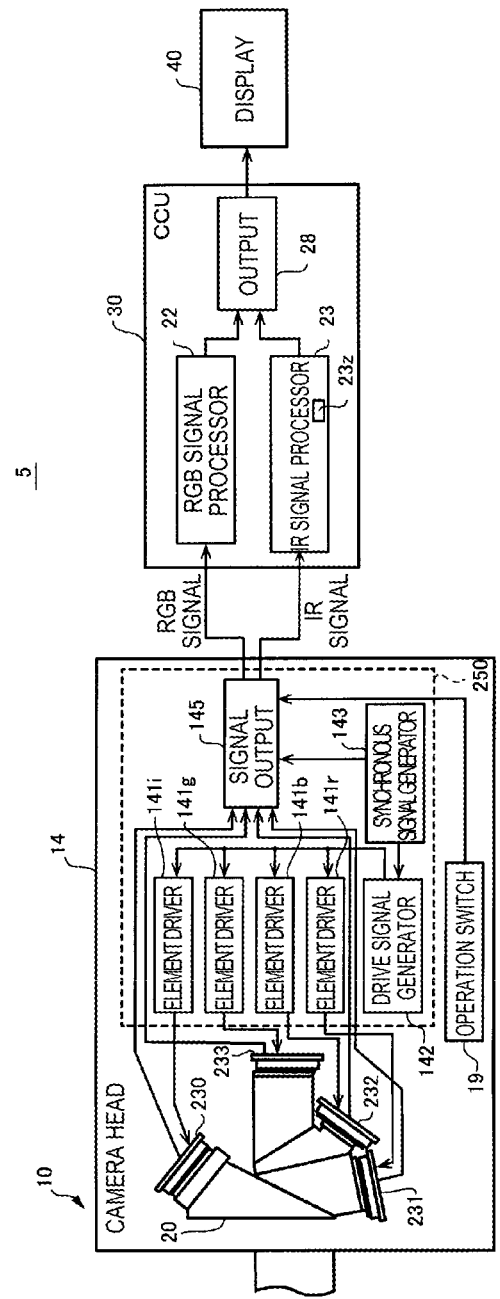
FIG. 5 is a block diagram illustrating an example of the configuration of an endoscopic system in the first exemplary embodiment.

Camera head 14 includes a housing which the user can grasp with a hand; four-color separation prism 20 (refer to FIG. 3); four image sensors 230, 231, 232, and 233 (refer to FIG. 3); and electronic substrate 250 (refer to FIG. 5).

Four-color separation prism 20 is a four-plane prism separating the light converged by relay lens 13 into three primary colors of light (R light (R component), G light (G component), and B light (B component)) and IR light (IR component). Image sensors 230 to 233 convert optical images, which are separated by four-color separation prism 20 and formed on the image-capturing surfaces, into image signals (electrical signals).

A charge coupled device (CCD), a complementary metal oxide semiconductor (CMOS), or the like is used as image sensors 230 to 233.

Four image sensors 230 to 233 are sensors respectively dedicated to receive IR component light, B component light, R component light, and G component light. Therefore, unlike a one plate camera receiving IR component light, R component light, G component light, and B component light via one image sensor, a small size sensor can be adopted as each individual image sensor. A ⅓ type (4.8 mm×3.6 mm) size image sensor is used. A one plate camera requires at least a ⅔ type (8.8 mm×6.6 mm) size image sensor.

A signal output circuit outputting a signal by a low-voltage differential signaling (LVDS) method, a timing generator circuit (TG circuit), and the like are mounted on electronic substrate 250 (refer to FIG. 5).

The signal output circuit outputs pulse type of RGB and IR signals for images captured by image sensors 230 to 233 by the low-voltage differential signaling (LVDS) method. The TG circuit supplies timing signals (synchronous signals) to inner components of camera head 14. The RGB signal is a signal containing at least one of the R, G, and B components.

Signal cable 14z for transmitting an image signal to camera control unit (CCU) 30 (to be described later) is mounted on camera head 14.

Configuration of Four-Color Separation Prism

Figure 3:
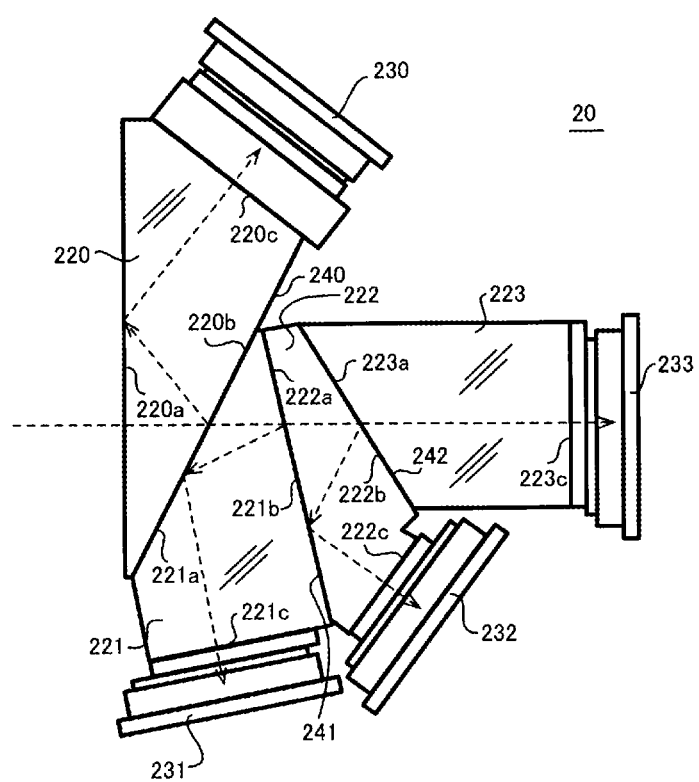
FIG. 3 is a schematic view illustrating an example of the structure of a four-color separation prism.

FIG. 3 is a view illustrating an example of the structure of four-color separation prism 20.

Four-color separation prism 20 separates incident light guided by relay lens 13 into three primary colors (R, G, and B components) of light, and IR component light. IR separation prism 220, blue color separation prism 221, red color separation prism 222, and green color separation prism 223 are sequentially assembled in four-color separation prism 20 in optical axial directions.

IR image sensor 230 is disposed to face light emitting surface 220c of IR separation prism 220. Blue color image sensor 231 is disposed to face light emitting surface 221c of blue color separation prism 221. Red color image sensor 232 is disposed to face light emitting surface 222c of red color separation prism 222. Green color image sensor 233 is disposed to face light emitting surface 223c of green color separation prism 223.

Image sensors 230 to 233 are CCD image sensors or CMOS image sensors including pixels arrayed in horizontal (H) and vertical (V) directions. Image sensors 230 to 233 convert optical images, which are formed on the image-capturing surfaces by the separated IR, R, G, and B component light, into electrical signals.

Light is incident to light incident surface 220a of IR separation prism 220. The light is reflected by reflective surface 220b facing light incident surface 220a. All the reflected light is then reflected at the boundary of light incident surface 220a of IR separation prism 220, emitted from light emitting surface 220c facing light incident surface 220a, and incident to IR image sensor 230. IR reflective film 240 is formed on reflective surface 220b by vapor deposition. IR separation prism 220 reflects the IR component light contained in the incident light, and allows the other component light (B, R, and G component light) to be transmitted therethrough. The light reflected by reflective surface 220b and light incident surface 220a is incident to and received by IR image sensor 230. As such, IR separation prism 220 is formed in order for light to travel through IR separation prism 220.

The light (incident light) transmitted through IR separation prism 220 is incident to light incident surface 221a of blue color separation prism 221. The light is reflected by reflective surface 221b facing light incident surface 221a. All the reflected light is then reflected at the boundary of light incident surface 221a of blue color separation prism 221, emitted from light emitting surface 221c facing light incident surface 221a, and incident to blue color image sensor 231. Blue color reflective film 241 is formed on reflective surface 221b by vapor deposition. Blue color separation prism 221 reflects the B component light contained in the incident light, and allows the other component light (R and G component light) to be transmitted therethrough. The light reflected by reflective surface 221b and light incident surface 221a is incident to and received by blue color image sensor 231. As such, blue color separation prism 221 is formed in order for light to travel through blue color separation prism 221.

The light (incident light) transmitted through blue color separation prism 221 is incident to light incident surface 222a of red color separation prism 222. The light is reflected by reflective surface 222b facing light incident surface 222a. All the reflected light is then reflected at the boundary of light incident surface 222a of red color separation prism 222, emitted from light emitting surface 222c facing light incident surface 222a, and incident to red color image sensor 232. Red color reflective film 242 is formed on reflective surface 222b by vapor deposition. Red color separation prism 222 reflects the R component light contained in the incident light, and allows the other component light (G component light) to be transmitted therethrough. The light reflected by reflective surface 222b and light incident surface 222a is incident to and received by red color image sensor 232. As such, red color separation prism 222 is formed in order for light to travel through red color separation prism 222.

The light (incident light) transmitted through red color separation prism 222 is incident to light incident surface 223a of green color separation prism 223, emitted from light emitting surface 223c facing light incident surface 223a, and then incident to green color image sensor 233. As such, green color separation prism 223 is formed in order for light to travel through green color separation prism 223.

IR image sensor 230 may output an electrical signal having each pixel value (signal level) without being processed, or may perform an H/V pixel addition process by which the pixel values of pixels adjacent to each other in the horizontal (H) and vertical (V) direction are added together, and output an electrical signal having a pixel value obtained by the H/V pixel addition process.

When the H/V pixel addition process is performed, the pixel value of the IR component in IR image sensor 230 is changed to "120" (=30×4) from approximately "30".

According to endoscope 10 in which IR image sensor 230 is independently provided in the exemplary embodiment, the pixel value of the IR component is changed to 3 to 12 times the pixel value (for example, approximately "10") of the IR component in the related art.

In the exemplary embodiment, the pixel values of B image sensor 231, R image sensor 232, and G image sensor 233 are deemed to be approximately "100". When the H/V pixel addition process is performed, the signal level of each of the R, G, and B components and the signal level of the IR component become equal to each other, and a user can easily observe an RGB image and an IR image. The RGB image is an image obtained from at least one signal of R, G, and B component signals. The IR image is an image obtained from an IR component signal.

Spectral Characteristics of Four-Color Separation Prism

Figure 4:
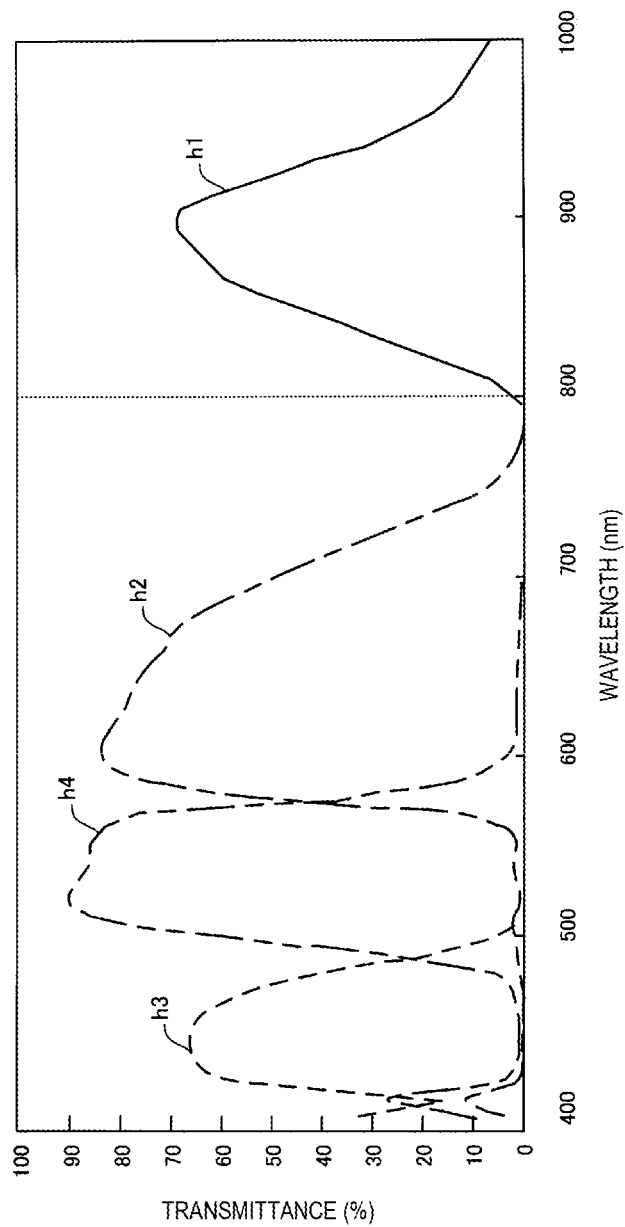
FIG. 4 is a graph illustrating an example of spectral characteristics of the four-color separation prism.

FIG. 4 is a graph illustrating an example of spectral characteristics of four-color separation prism 20. In FIG. 4, the vertical axis represents the transmittance (%) which is equivalent to a ratio between the amount of light incident to the prisms and the amount of light incident to image sensors 230 to 233 corresponding to the prisms. In FIG. 4, the horizontal axis represents the wavelength (nm) of light incident to each of image sensors 230 to 233.

In FIG. 4, waveform h1 (illustrated by the solid line) represents spectral characteristics of IR component light incident to IR image sensor 230. The IR component light contained in the light incident to four-color separation prism 20, which is incident to IR image sensor 230, has a waveform with a wavelength of 800 nm to 1000 nm having a peak transmittance of approximately 70% in the vicinity of a wavelength of 900 nm.

Waveform h2 (illustrated by the alternate long and short-dashed line) represents spectral characteristics of the R component light incident to red image sensor 232. The R component light incident to red image sensor 232 has a waveform having a peak transmittance of approximately 80% in the vicinity of a wavelength of 600 nm.

Waveform h3 (illustrated by the dotted line) represents spectral characteristics of the B component light incident to blue image sensor 231. The B component light incident to blue image sensor 231 has a waveform, the peak transmittance of which exceeds 60% in the vicinity of a wavelength of 450 nm.

Waveform h4 (illustrated by the alternating one long and two short-dashed line) represents spectral characteristics of the G component light incident to green image sensor 233. The G component light incident to green image sensor 233 has a waveform having a peak transmittance of approximately 90% in the vicinity of a wavelength of 530 nm.

As such, the transmittance of all the IR, R, B, and G component light separated by four-color separation prism 20 exceeds 60%. Accordingly, the pixel values of the IR, R, B, and G components are suitably obtained without considerably amplifying the IR component signal. As a result, when an image of a diseased site is captured, the color reproductivity of the captured image containing the IR component is improved.

Configuration of Endoscopic System

FIG. 5 is a block diagram illustrating the configuration of endoscopic system 5. Endoscopic system 5 is configured to include endoscope 10; CCU 30; and display 40. Camera head 14 of endoscope 10 includes four-color separation system 20 and image sensors 230, 231, 232, and 233. In FIG. 5, camera head 14 further includes element drivers 141i, 141r, 141b, and 141g; drive signal generator 142; synchronous signal generator 143; and signal output 145.

Element driver 141i drives image sensor 230 according to a drive signal. Element driver 141r drives image sensor 231 according to a drive signal. Element driver 141b drives image sensor 232 according to a drive signal. Element driver 141g drives image sensor 233 according to a drive signal.

Drive signal generator 142 generates a drive signal for each of element drivers 141i, 141r, 141b, and 141g. Synchronous signal generator 143 is equivalent to a timing generator (TG) open-path from the perspective of function, and supplies a synchronous signal (timing signal) to drive signal generator 142 and the like.

Signal output 145 transmits electrical signals from image sensors 230, 231, 232, and 233 to CCU 30 via signal cable 14z by the LVDS method. Signal output 145 may transmit a synchronous signal from synchronous signal generator 143 to CCU 30 via signal cable 14z. Signal output 145 may transmit an operation signal from operation switch 19 to CCU 30 via signal cable 14z. Signal output 145 is equivalent to a signal output circuit from the perspective of function.

CCU 30 realizes various functions by executing a program held in an internal memory of CCU 30 or an external memory (not illustrated). The various functions include the functions of RGB signal processor 22, IR signal processor 23, and output 28.

RGB signal processor 22 converts electrical signals for the B, R, and G components from image sensors 231, 232, and 233 into image signals which can be displayed on display 40, and outputs the converted image signals to output 28.

IR signal processor 23 converts an electrical signal for the IR component from image sensor 230 into an image signal, and outputs the converted image signal to output 28. IR signal processor 23 may include gain adjustor 23z. Gain adjustor 23z adjusts a gain when an electrical signal for the IR component from IR image sensor 230 is converted into an image signal. Gain adjustor 23*z* may perform adjustment such that the signal strength of the RGB component image signal is substantially the same as the signal strength of the IR component image signal.

A user can reproduce an IR image having arbitrary strength with respect to an RGB image using gain adjustor 23*z*. Instead of the gain of the electrical signal for the IR component being adjusted, or together with the adjustment of the gain of the electrical signal for the IR component, RGB signal processor 22 may adjust the gain of the electrical signals for the RGB component.

During signal processing, RGB signal processor 22 and IR signal processor 23 receive a synchronous signal from synchronous signal generator 143, and are operated according to the synchronous signal. Accordingly, the R, G, and B color component images and the IR component image are adjusted such that there is no timing offset therebetween.

Output 28 outputs at least one of the R, G, and B color component image signals and the IR component image signal to display 40 according to the synchronous signal from synchronous signal generator 143. Output 28 outputs an image signal based on either a dual output mode or a superimposed output mode.

In the dual output mode, output 28 outputs RGB image G1 and IR image G2 (refer to FIG. 6) on separate screens at the same time. In the dual output mode, a user can observe diseased site tg while comparing the RGB image and the IR image on the separate screens to each other.

In the superimposed output mode, output 28 outputs combined image GZ in which an RGB image and an IR image are superimposed on each other. In the superimposed output mode, a user can clearly observe diseased site tg that emits fluorescent light in the RGB image due to ICG and IR light (illumination light)

In this example, a processor in CCU 30 processes RGB signal processor 22, IR signal processor 23, and output 28 software-wise in collaboration with the memory; however, each of RGB signal processor 22, IR signal processor 23, and output 28 may be formed by dedicated hardware.

The screen of display 40 displays an image of an object (for example, diseased site tg), which is captured by endoscope 10 and output from CCU 30, based on an image signal from CCU 30. In a dual output mode, display 40 divides a screen into multiple screens (for example, two screens), and displays RGB image G1 and IR image G2 side by side on the respective screens (refer to FIG. 6). In a superimposed output mode, display 40 displays combined image GZ, in which RGB image G1 and IR image G2 are superimposed on each other, on one screen (refer to FIG. 7).

In endoscopic system 5, indocyanine green (ICG) (fluorescent substance) may be injected into the body, a site (diseased site) (for example, tumor) in the body containing the excessively accumulated fluorescent substance may be irradiated with near-infrared light, and an image of the site may be captured using endoscope 10.

Light L introduced to light source connector 18 by the user's operation of operation switch 19 is guided to the distal end of scope 11, projected onto a site containing a diseased site and the surroundings thereof from image-capturing window 11*z*, and illuminates the site. Light reflected by the diseased site is guided to a rear end of scope 11 via image-capturing window 11*z*, converged by relay lens 13, and incident to four-color separation prism 20 of camera head 14.

IR component light separated from the incident light by IR separation prism 220 is captured as an infrared light component of an optical image by IR image sensor 230 of four-color separation prism 20. B component light separated by blue color separation prism 221 is captured as a blue color component of an optical image by blue image sensor 231. R component light separated by red color separation prism 222 is captured as a red color component of an optical image by red image sensor 232. G component light separated by green color separation prism 223 is captured as a green color component of an optical image by green image sensor 233.

An electrical signal for the IR component converted by IR image sensor 230 is converted into an image signal by IR signal processor 23 in CCU 30, and is output by output 28. Electrical signals for the B, R, and G components converted by visible-light image sensors 231, 232, and 233 are converted into image signals by RGB signal processor 22 in CCU 30, and are output by output 28. The IR component image signal, and the B, R, and G component image signals are output to display 40 in a synchronous mode.

Figure 6:
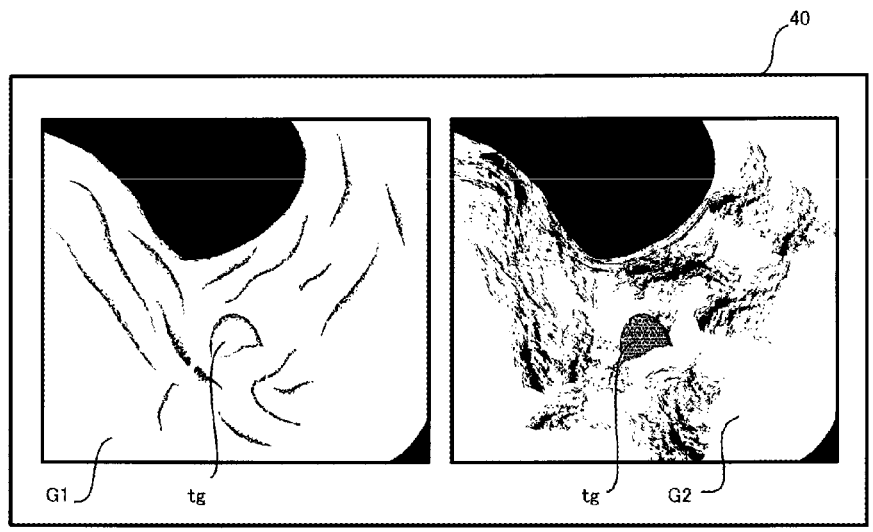
FIG. 6 shows schematic views illustrating an example of an image which is displayed on a display in a dual output mode.

When output 28 is set to a dual output mode, display 40 displays RGB image G1 and IR image G2 on two screens at the same time. FIG. 6 shows schematic views illustrating images displayed on display 40 in a dual output mode. RGB image G1 is a color image obtained by irradiating a site containing diseased site tg with visible light and capturing an image of the site. IR image G2 is a black and white image (can be set to an arbitrary color) obtained by irradiating a site containing diseased site tg with IR light and capturing an image of the site.

Figure 7:
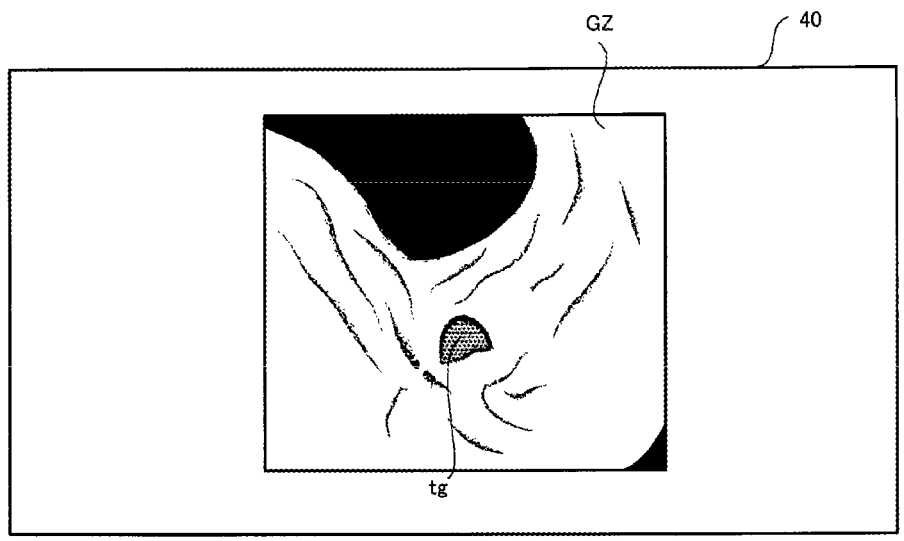
FIG. 7 is a schematic view illustrating an example of an image which is displayed on the display in a superimposed output mode.

When output 28 is set to a superimposed output mode, display 40 displays combined image GZ in which RGB image G1 and IR image G2 are superimposed (combined together) on each other. FIG. 7 is a schematic view illustrating an image displayed on display 40 in a superimposed output mode.

Effects

Four-color separation prism 20 is used in endoscope 10, and IR image sensor 230 receives IR light emitted from IR separation prism 220 having a high transmittance with respect to IR light. Therefore, in endoscope 10, the amount of IR light received can be increased. As a result, it is not necessary to excessively amplify an IR component signal, and it is possible to suppress degradation of quality of an image to which the IR component is added and which is captured by endoscope 10.

It is possible to reduce the size of an image sensor compared to an image sensor in a one plate camera, and to reduce the size of endoscope 10 by using four-color separation prism 20. The size of an image sensor in a one plate camera is 1 inch or 38 mm, and the size of each of image sensors 230 to 233 in the exemplary embodiment is less than or equal to ⅓ inch.

Since an IR cut filter is not used in four-color separation prism 20, endoscopic system 5 is capable of outputting an RGB image and an IR image at the same time. Therefore, a user can confirm the entire site containing a diseased site of a patient in the RGB image, and the diseased site emitting fluorescent light in the IR image, and easily recognize the position of the diseased site in the surroundings thereof. The RGB image is an RGB component image, and the IR image is an IR component image.

IR image sensor 230 converting IR component light into an electrical signal may perform an H/V pixel addition process, and output an electrical signal having an added pixel value. Accordingly, endoscope 10 is capable of further increasing the signal strength of the IR component, and further emphasizing an IR component image displayed on display 40, and a user can easily recognize a diseased site.

In endoscopic system 5, the gain may be adjusted such that the signal strength of each of the R, G, and B components and the signal strength of the IR component are substantially equal to each other. In this case, it is possible to set the pixel value of each of the R, G, and B components to be equal to the pixel value of the IR component, and to obtain an easy-to-see image.

In endoscopic system 5, the gain may be adjusted such that there is a difference between the signal strength of each of the R, G, and B components and the signal strength of the IR component. In this case, endoscopic system 5 is capable of displaying an RGB image and an IR image having a user's desired image quality.

When four-color separation prism 20 is used, the signal strength of the IR component incident to the IR image sensor is increased compared to when a three-color separation prism is used. Therefore, the difference between the pixel value of the RGB component and the pixel value of the IR component is decreased, and thus it is possible to reproduce well-balanced RGB and IR component colors without excessively amplifying an electrical signal output from IR image sensor 230 using CCU 30. Accordingly, in endoscopic system 5, an image containing clear RGB and IR components is obtained while the amplification of noise is suppressed.

When an RGB image and an IR image are displayed on two screens at the same time, a user can compare and confirm both images, and user friendliness is improved.

When an RGB image and an IR image are disposed on one screen while being superimposed on each other, a user can confirm an RGB component image and an IR component image in one image, and user friendliness is improved.

Other Exemplary Embodiments

The first exemplary embodiment has been described as an example of the technology in this disclosure. However, the technology in this disclosure is not limited to the first exemplary embodiment, and can be applied to exemplary embodiments realized by making changes, replacements, additions, omissions, or the like to the first exemplary embodiment.

In the first exemplary embodiment, a rigid endoscope is exemplified as endoscope 10; however, another rigid endoscope with a different configuration or a flexible endoscope may be used insofar as four-color separation prism 20 is used.

In the first exemplary embodiment, ICG as an example of an optical contrast agent is injected into the living body; however, optical contrast agents other than ICG may be injected into the living body. In this case, spectral characteristics of non-visible light in the wavelength region may be determined according to the wavelength of excitation light for exciting the optical contrast agent.

In the first exemplary embodiment, a medicine emitting fluorescent light in the wavelength region of infrared light is used; however, a medicine emitting fluorescent light in the wavelength region of ultraviolet light may be used. Also in this case, similar to the case in which an optical contrast agent emitting fluorescent light in the near-infrared region is used, an endoscope is capable of capturing an image of a diseased site emitting fluorescent light.

In the first exemplary embodiment, IR separation prism 220, blue color separation prism 221, red color separation prism 222, and green color separation prism 223 are exemplarily disposed in four-color separation prism 20 sequentially from a light incidence side; however, another sequence of disposition may be adopted.

In the first exemplary embodiment, CCU 30 is described as an example of a processor. A processor may have any physical configuration insofar as the processor is capable of controlling endoscopic system 5. Accordingly, a processor is not limited to CCU 30. When programmable CCU 30 is used, it is possible to change process content by changing a program, resulting in an improvement in the degree of freedom in designing a processor. A processor may be formed of one semiconductor chip, or may be physically formed of multiple semiconductor chips. When a processor is formed of multiple semiconductor chips, control in the first exemplary embodiment may be realized by the separate corresponding semiconductor chips. In this case, it can be deemed that one processor is formed of the multiple semiconductor chips. A processor may be formed of a member (capacitor or the like) having a function different from that of a semiconductor chip. A processor may be formed of one semiconductor chip by which the function of a processor and other functions are realized. When a programmable circuit is mounted on electronic substrate 250, it is possible to change process content by changing a program. The number of circuits may be one, or more than one.

The invention claimed is:

1. An endoscope prism comprising:
   a four-color separation prism comprising an infrared separation prism, a second color separation prism, a third color separation prism and a fourth color separation prism, an order of the infrared separation prism, the second color separation prism, the third color separation prism and the fourth color separation prism from a distal end of the four-color separation prism being the infrared separation prism, the second color separation prism, the third color separation prism and the fourth color separation prism, the third color separation prism including a light incident surface which, in operation, reflects a red component of the light from an object, the light incident surface of the third color separation prism being adjacent a light reflective surface of the second color separation prism,
   wherein the light incident surface of the third color separation prism is coextensive with the light reflective surface of the second color separation prism.

2. The endoscope prism of claim 1, wherein the light reflective surface of the second color separation prism, in operation, reflects a blue component of the light from an object.

3. The endoscope prism of claim 2, wherein the infrared separation prism includes a light incident surface,
   the light reflective surface of the second color separation prism arranged relative to the light incident surface of the infrared separation prism such that a first angle is formed between the light incident surface of the infrared separation prism and the light reflective surface of the second color separation prism, and
   the third color separation prism includes a light reflective surface arranged relative to the light incident surface of the infrared separation prism such that a second angle is formed between the light incident surface of the infrared separation prism and the light reflective surface of the third separation prism, the first angle being less than the second angle.

4. The endoscope prism of claim 3, wherein the infrared separation prism includes a light reflective surface arranged relative to the light incident surface of the infrared separation prism such that a third angle is formed between the light incident surface of the infrared separation prism and the light reflective surface of the infrared separation prism, the first angle being less than the third angle.

5. The endoscope prism of claim 1, wherein the light reflective surface of the second color separation prism, in operation, reflects a green component of the light from an object.

6. The endoscope prism of claim 5, wherein the infrared separation prism includes a light incident surface,
   the light reflective surface of the second color separation prism arranged relative to the light incident surface of the infrared separation prism such that a first angle is formed between the light incident surface of the infrared separation prism and the light reflective surface of the second color separation prism, and
   the third color separation prism includes a light reflective surface arranged relative to the light incident surface of the infrared separation prism such that a second angle is formed between the light incident surface of the infrared separation prism and the light reflective surface of the third color separation prism, the first angle being less than the second angle.

7. The endoscope prism of claim 6, wherein the infrared separation prism includes a light reflective surface arranged relative to the light incident surface of the infrared separation prism such that a third angle is formed between the light incident surface of the infrared separation prism and the light reflective surface of the infrared separation prism, the first angle being less than the third angle.

8. An endoscope prism comprising:
   a four-color separation prism comprising an infrared separation prism, a second color separation prism, a third color separation prism and a fourth color separation prism, an order of the infrared separation prism, the second color separation prism, the third color separation prism and the fourth color separation prism from a distal end of the four-color separation prism being the infrared separation prism, the second color separation prism, the third color separation prism and the fourth color separation prism,
   the third color separation prism including a light incident surface which, in operation, reflects a blue component of the light from an object, the light incident surface of the third color separation prism being adjacent a light reflective surface of the second color separation prism,
   wherein the light incident surface of the third color separation prism is coextensive with the light reflective surface of the second color separation prism.

9. The endoscope prism of claim 8, wherein the light reflective surface of the second color separation prism, in operation, reflects a green component of the light from an object.

10. The endoscope prism of claim 9, wherein the infrared separation prism includes a light incident surface,
    the light reflective surface of the second color separation prism arranged relative to the light incident surface of the infrared separation prism such that a first angle is formed between the light incident surface of the infrared separation prism and the light reflective surface of the second color separation prism, and
    the third color separation prism includes a light reflective surface arranged relative to the light incident surface of the infrared separation prism such that a second angle is formed between the light incident surface of the infrared separation prism and the light reflective surface of the third color separation prism, the first angle being less than the second angle.

11. The endoscope prism of claim 10, wherein the infrared separation prism includes a light reflective surface arranged relative to the light incident surface of the infrared separation prism such that a third angle is formed between the light incident surface of the infrared separation prism and the light reflective surface of the infrared separation prism, the first angle being less than the third angle.

12. The endoscope prism of claim 8, wherein the light reflective surface of the second color separation prism, in operation, reflects a red component of the light from an object.

13. The endoscope prism of claim 12, wherein the infrared separation prism includes a light incident surface,
    the light reflective surface of the second color separation prism arranged relative to the light incident surface of the infrared separation prism such that a first angle is formed between the light incident surface of the infrared separation prism and the light reflective surface of the second color separation prism, and
    the third color separation prism includes a light reflective surface arranged relative to the light incident surface of the infrared separation prism such that a second angle is formed between the light incident surface of the infrared separation prism and the light reflective surface of the third color separation prism, the first angle being less than the second angle.

14. The endoscope prism of claim 13, wherein the infrared separation prism includes a light reflective surface arranged relative to the light incident surface of the infrared separation prism such that a third angle is formed between the light incident surface of the infrared separation prism and the light reflective surface of the infrared separation prism, the first angle being less than the third angle.

15. An endoscope prism comprising:
    a four-color separation prism comprising an infrared separation prism, a second color separation prism, a third color separation prism and a fourth color separation prism, an order of the infrared separation prism, the second color separation prism, the third color separation prism and the fourth color separation prism from a distal end of the four-color separation prism being the infrared separation prism, the second color separation prism, the third color separation prism and the fourth color separation prism,
    the third color separation prism including a light incident surface which, in operation, reflects a green component of the light from an object, the light incident surface of the third color separation prism being adjacent a light reflective surface of the second color separation prism
    wherein the light incident surface of the third color separation prism is coextensive with the light reflective surface of the second color separation prism.

16. The endoscope prism of claim 15, wherein the light reflective surface of the second color separation prism, in operation, reflects a red component of the light from an object.

17. The endoscope prism of claim 16, wherein the infrared separation prism includes a light incident surface,
    the light reflective surface of the second color separation prism arranged relative to the light incident surface of the infrared separation prism such that a first angle is formed between the light incident surface of the infrared separation prism and the light reflective surface of the second color separation prism, and
    the third color separation prism includes a light reflective surface arranged relative to the light incident surface of the infrared separation prism such that a second angle is formed between the light incident surface of the infrared separation prism and the light reflective surface of the third color separation prism, the first angle being less than the second angle.

18. The endoscope prism of claim 17, wherein the infrared separation prism includes a light reflective surface arranged relative to the light incident surface of the infrared separation prism such that a third angle is formed between the light incident surface of the infrared separation prism and the light reflective surface of the infrared separation prism, the first angle being less than the third angle.

19. The endoscope prism of claim 15, wherein the light reflective surface of the second color separation prism, in operation, reflects a blue component of the light from an object.

20. The endoscope prism of claim 19, wherein the infrared separation prism includes a light incident surface,
   the light reflective surface of the second color separation prism arranged relative to the light incident surface of the infrared separation prism such that a first angle is formed between the light incident surface of the infrared separation prism and the light reflective surface of the second color separation prism, and
   the third color separation prism includes a light reflective surface arranged relative to the light incident surface of the infrared separation prism such that a second angle is formed between the light incident surface of the infrared separation prism and the light reflective surface of the third color separation prism, the first angle being less than the second angle.

* * * * *